US009213106B2

(12) United States Patent
Miller

(10) Patent No.: US 9,213,106 B2
(45) Date of Patent: Dec. 15, 2015

(54) METHOD OF MEASURING LUMINESCENCE OF A MATERIAL

(75) Inventor: Steven D. Miller, Richland, WA (US)

(73) Assignee: BATTELLE MEMORIAL INSTITUTE, Richland, WA (US)

(*) Notice: Subject to any disclaimer, the term of this patent is extended or adjusted under 35 U.S.C. 154(b) by 724 days.

(21) Appl. No.: 13/449,607

(22) Filed: Apr. 18, 2012

(65) Prior Publication Data

US 2012/0313011 A1 Dec. 13, 2012

Related U.S. Application Data

(60) Provisional application No. 61/494,796, filed on Jun. 8, 2011.

(51) Int. Cl.
| | |
|---|---|
| *G01N 21/64* | (2006.01) |
| *G01T 1/10* | (2006.01) |
| *G21K 5/00* | (2006.01) |
| *G01J 1/58* | (2006.01) |
| *G01T 1/11* | (2006.01) |
| *G01T 1/105* | (2006.01) |

(52) U.S. Cl.
CPC ... *G01T 1/11* (2013.01); *G01T 1/10* (2013.01); *G01T 1/105* (2013.01); *G01J 1/58* (2013.01); *G01N 21/64* (2013.01); *G21K 5/00* (2013.01)

(58) Field of Classification Search
CPC ..... G21K 5/00; G01N 21/64; G01N 21/6402; G01N 21/6408; G01J 1/58
See application file for complete search history.

(56) References Cited

U.S. PATENT DOCUMENTS

| 5,567,948 A * | 10/1996 | Miller ......................... 250/484.5 |
| 5,569,927 A | 10/1996 | Miller |
| 5,731,590 A | 3/1998 | Miller |
| 6,531,217 B1 * | 3/2003 | Martin et al. .................. 428/364 |
| 7,675,045 B1 * | 3/2010 | Werner ............... G01N 21/6408 250/458.1 |
| 2002/0064789 A1 * | 5/2002 | Weiss ..................... B82Y 15/00 435/6.14 |
| 2005/0059681 A1 * | 3/2005 | Cremer ............... G01N 21/6428 514/260.1 |
| 2008/0032414 A1 * | 2/2008 | Zhuang .............. G01N 21/6428 436/172 |
| 2008/0182336 A1 * | 7/2008 | Zhuang .............. G01N 21/6428 436/172 |
| 2009/0125242 A1 * | 5/2009 | Choi ....................... G01N 21/45 702/19 |
| 2012/0325112 A1 * | 12/2012 | Gregoratti et al. ......... 106/31.65 |

FOREIGN PATENT DOCUMENTS

WO 9300595 A1 1/1993

OTHER PUBLICATIONS

Ogorodnikov, I. N., Pustovarov, V. A., Kruzhalov, A. V., Isaenko, L. I., Kirm, M., & Zimmerer, G. Electronic excitations and luminescence in non-linear alkali borate crystals.*

(Continued)

*Primary Examiner* — Casey Bryant
(74) *Attorney, Agent, or Firm* — A. J. Gokcek

(57) ABSTRACT

A method of measuring luminescence of a material is disclosed. The method includes applying a light source to excite an exposed material. The method also includes amplifying an emission signal of the material. The method further includes measuring a luminescent emission at a fixed time window of about 10 picoseconds to about 10 nanoseconds. The luminescence may be radio photoluminescence (RPL) or optically stimulated luminescence (OSL).

18 Claims, 2 Drawing Sheets

(56) References Cited

OTHER PUBLICATIONS

Ravotti, F., et al. "Time-resolved photoluminescence and optically stimulated luminescence measurements of picosecond-excited SrS: Ce, Sm phosphor." Journal of Applied Physics 102.12 (2007): 123102.*

Fan, Wenhui, et al. "Picosecond infrared laser stimulation of luminescence in CaS: Eu, Sm." Journal of applied physics 85.1 (1999): 451-454.*

Vicidomini et al. "Sharper Low-Power STED Nanoscopy by Time Gating", Nature Methods, (7), Jul. 2011, p. 571-573.*

Miller, S. D., et al., Laser-Induced Optically Stimulated M Centre Luminescence in LIF, Radiation Protection Dosimetry, 33, 1990, 59-62.

Regulla, D. F., Lithium Fluoride Dosimetry Based on Radiophotoluminescence, Health Physics, 22, 1972, 491-496.

Murphy, M. K., et al., Dose response and post-irradiation characteristics of the Summa 535-nm photo-fluorescent film dosimeter, Radiation Physics and Chemistry, 68, 2003, 981-994.

Murphy, M. K, et al., Sunna 535-nm photo-fluorescent film dosimeter response to different environmental conditions, Radiation Physics and Chemistry, 68, 2003, 995-1003.

Miller, S. D., High Dose Dosimetry Using Optically Stimulated Luminescence, Radiation Protection Dosimetry, 66, 1996, 201-204.

International Search Report and Written Opinion for International Application No. PCT/US2012/039508, International Filing Date May 25, 2012, Date of Mailing Jan. 21, 2013.

Ondic, L., et al., Data Processing Correction of the Irising Effect of a Fast-Gating Intensified Charge-Coupled Device on Laser-Pulse-Excited Luminescence Spectra, Review of Scientific Instruments, AIP, Melville, NY, US, vol. 81, No. 6, Jun. 9, 2010, pp. 63104-1-63104-5.

Ankjaergaard, C., et al., Optimising the Separation of Quartz and Feldspar Optically Stimulated Luminescence Using Pulsed Excitation, Radiation Measurements, Elsevier, Amsterdam, NL, vol. 45, No. 7, Aug. 1, 2010, pp. 778-785.

* cited by examiner

METHOD OF MEASURING LUMINESCENCE OF A MATERIAL

CROSS-REFERENCE TO RELATED APPLICATIONS

This application claims priority from U.S. Provisional Patent Application Ser. No. 61/494,796 and entitled "METHOD FOR RED-SHIFTING THE OSL OUTPUT IN COMPOSITE OSL MATERIALS AND APPLICATIONS THEREOF, which is hereby incorporated by reference in its entirety for all purposes.

STATEMENT REGARDING FEDERALLY SPONSORED RESEARCH OR DEVELOPMENT

The invention was made with Government support under Contract DE-AC05-76RL01830, awarded by the U.S. Department of Energy. The Government has certain rights in the invention.

TECHNICAL FIELD

This invention relates to measuring luminescence of a material. More specifically, this invention relates to measuring luminescence of a material by applying a light source to excite a material and measuring emission at a fixed time window, which minimizes background noise not related to a luminescent response of the material.

BACKGROUND OF THE INVENTION

Optically stimulated luminescence (OSL) and radio photoluminescence (RPL) are methods used for measuring doses from ionizing radiation. In typical arrangements, a device or material is optically stimulated and then emits luminescence (photons) as a result of the optical stimulation that is proportional to the ionizing radiation dose. Photons are detected using a sensitive light detector, such as a photomultiplier tube, and the signal from the detector is then used to calculate the dose that the material has absorbed.

Maximizing the signal-to-noise ratio (SNR) of the optical measurements is one of the main challenges in luminescence dosimetry. The major difficulty with achieving very high signal-to-noise ratios (SNR) at the extremely low ionizing radiation doses required for modern personnel dosimetry is the ability to minimize and ultimately reject background signals that are not related to the luminescence emission that is proportional to the ionizing radiation exposure.

As an example of the background noise problem, an OSL or RPL material, such as lithium fluoride (LiF) powder combined with a binder or polymer, introduces two sources of unwanted background luminescence that interferes with the measurement of the true OSL or RPL response and raises the minimum-detectable-dose (MDD) achievable with the composite dosimeter. During the optical stimulation process the optimal excitation light, blue light in the case of macro LiF, stimulates unwanted non-ionizing-radiation-dose-dependent emission light that partially overlaps the emission wavelengths of interest. Unwanted background fluorescence emanates from the LiF powder itself (both within the LiF crystal grain and also the surfaces of the LiF grains) and from the polymer. Optical bandpass filters placed adjacent to the light detector are selected to optimize the amount of good light emission reaching the light detector, while rejecting the majority of the out-of-band unwanted background light.

Despite very careful engineering of OSL reader systems, LiF polyethylene dosimeters (circa the late 2000s) still cannot measure much less than a few Gy due primarily with the fact that the sources of unwanted fluorescence overlap with the OSL emission band. What is needed is a new method of rejecting unwanted background fluorescence to achieve higher SNR in a composite material dosimeter.

SUMMARY OF THE INVENTION

The present invention is directed to methods of measuring luminescence of a material, methods of reducing background fluorescence of a material, and methods of altering properties of a luminescent material.

In one embodiment, a method of measuring luminescence of a material is disclosed. The method includes applying a light source to excite an exposed material; amplifying an emission signal of the material; and measuring a luminescent emission at a fixed time window of about 10 picoseconds to about 10 nanoseconds.

In one embodiment, the luminescence is radio photoluminescence or optically stimulated luminescence (OSL).

The material may be, but is not limited to, one of the following: an alkali halide material, an alkali earth halide material, a polymer material, a ceramic material, a crystalline or semi-crystalline material, glass, or combinations thereof. The material can further include glues and/or adhesives.

In one embodiment, the alkali halide material is lithium fluoride. In another embodiment, the alkali halide material is, but not limited to, at least one of the following: sodium fluoride, a bromide, a chloride, and an iodide.

In one embodiment, the material is combined with a polymer. In another embodiment, the material is in the size range of approximately 10 nanometers to approximately 500 micrometers.

In one embodiment, the method further comprises filtering to isolate a desired range of emission wavelengths.

In one embodiment, an excitation pulse of the light source is shorter than a decay time constant of the material. The decay time constant is a sub-nano-second decay constant in the range of 100 to 300 picoseconds. In one embodiment, the excitation pulse of the light source is an approximately 10 picosecond to 300 picosecond wide pulse. The light source may be a laser, a light-emitting diode (LED), or a flash lamp.

In one embodiment, a train of light pulses is applied repeatedly to quantify a radiation dose imparted to the material.

In one embodiment, the exposed material is an irradiated material.

In another embodiment of the present invention, a method of reducing background fluorescence of a material is disclosed. The method comprises applying a light source to excite an exposed material; and saturating the background fluorescence as a function of both the time-width of an excitation pulse of the light source and peak-power of the excitation pulse. The background fluorescence is non-ionizing radiation dose dependent.

The material is, but not limited to, at least one of the following: a polymer, an adhesive, ceramics, wax, glue, glass, and a translucent material. In another embodiment, the material is an alkali halide material combined with a polymer.

In another embodiment of the present invention, a method of altering properties of a luminescent material is disclosed. The method comprises preparing the luminescent material to a size range of approximately 1 to 2,000 nanometers; irradiating the material; and exciting the irradiated material with a light source to measure at least one of the following altered properties of the material: excitation curves, emission curves, and a time constant of a luminescent emission of the material. The time constant can include more than one time constant.

In one embodiment, the luminescent material comprises an alkali halide material, an alkali earth halide material, a polymer material, a ceramic material, a crystalline or semi-crystalline material, glass, and combinations thereof material comprises an alkali halide material combined with a polymer. The alkali halide material may be lithium fluoride or at least one of the following: sodium fluoride, a bromide, a chloride, an iodide, or an alkali earth halide.

In one embodiment, the preparing the luminescent material to a size range of approximately 1 to 2,000 nanometers comprises grinding the luminescent material to a size range of approximately 1 to 2,000 nanometers.

In one embodiment, the light source is a laser, a LED, or a flash lamp.

In another embodiment of the present invention, a method of altering properties of a luminescent material is disclosed. The method comprises preparing the luminescent material to a size range of approximately 1 to 2,000 nanometers; and exciting the luminescent material with a light source to measure at least one of the following altered properties of the material: excitation curves, emission curves, and a time constant of a luminescent emission of the material. The time constant can include more than one time constant. The luminescent material may be any fluorescent material.

DETAILED DESCRIPTION OF THE PREFERRED EMBODIMENTS

The present invention is directed to methods of measuring luminescence of a material, methods of reducing background fluorescence of a material, and methods of altering properties of a luminescent material.

In one embodiment, a method of achieving higher signal-to-noise ratio (SNR) in a composite material dosimeter is disclosed. The method includes time-gating the OSL or RPL response emission and rejecting the unwanted background fluorescence irrespective of its source. This emission process is optimally stimulated through the use of a fast laser pulse, LED or a flash lamp—fast being less than the time-constant of the OSL (or RPL) emission process being targeted—applied to an exposed material. The emission signal of the exposed material is then amplified and measured at a fixed time window or interval on the order of a half-life of the decay constant of the material. This process can be repeated for hundreds to thousands of pulses or more. Since ultra-fast pulsed lasers, LEDs and flash lamps generally are available in high repetition rates, the ability to collect thousands of averaged signals over narrow fixed time-intervals can be accomplished in a few seconds or less.

Figure 1:
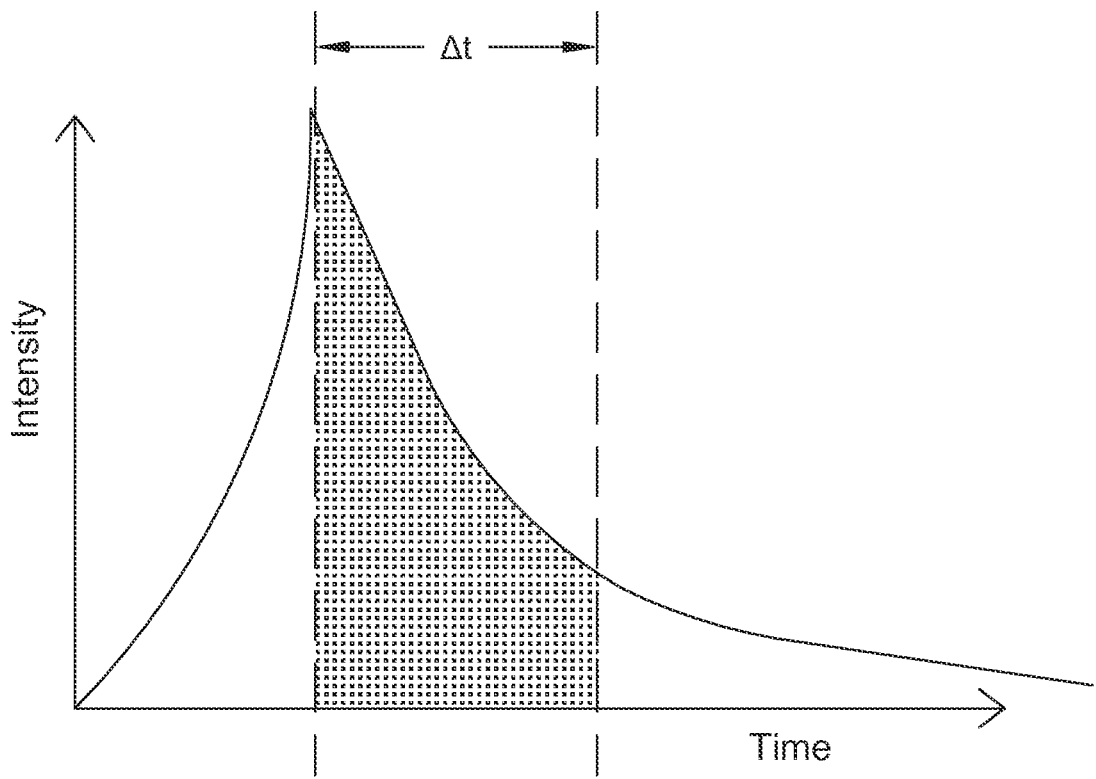
FIG. 1 shows intensity decay over time by applying a laser source to an exposed material and measuring a luminescent emission at a fixed time window ($\Delta t$), in accordance with one embodiment of the present invention.

FIG. 1 shows intensity decay over time by applying a light source to an exposed material and measuring a luminescent emission at a fixed time window ($\Delta t$), in accordance with one embodiment of the present invention. The width of the excitation pulse is shorter than the decay time constant of the exposed material.

The improvement to SNR using this measurement technique is significant. For example, in the area of OSL, assuming that both the OSL emission and the unwanted background fluorescence follow normal exponential decay mechanisms then modeling a fixed collection time interval of 100 picoseconds and assuming a background fluorescence time constant of a few hundred nano-seconds, improvement to the SNR can be over 1 million and up to a billion or more in certain optimal circumstances. Optimal binder materials and readout parameters are also selected for these dosimeter applications.

Besides selecting binders or polymers to combine with an OSL material, which can be a lithium fluoride (LiF) powder, that have very slow fluorescence decay constants, binders may be selected that emit their luminescence or fluorescence outside the OSL emission band and whose fluorescence becomes saturated at low excitation intensities.

As mentioned above, unwanted fluorescence can be eliminated by the methods described above. Another method to minimize unwanted background fluorescence is through the selection of materials and/or binders that display rapid saturations of their fluorescence as a function of both the time-width of the excitation pulse and the peak-power of the excitation pulse. For example, by exciting a composite material LiF dosimeter with a high-peak power pico-second laser pulse and measuring for, say, a few hundred pico-seconds, the unwanted background noise will be eliminated by at least two mechanisms: 1. The exponential decay mathematics of two different time-constant decay mechanisms, and 2. The rapid saturation and therefore suppression of unwanted background fluorescence due to high peak power and ultra-short laser excitation.

Ultrafast-fluorescence also enables a much improved security phosphor for use as an optical security taggant and as a high density data storage material. As an optical security taggant, the enhancement of the faster emission properties enhances the possible optical signatures available. By time-gating the light detection, the OSL signal can be measured with the room-lights on. Normally OSL detection of very low radiation doses needed to be done in a light-tight enclosure. With a sub-nano-second decay constant, a hand-held OSL reader device can send a very fast pulse or train of pulses and the OSL emission return can be time-gated to only measure and amplify the very short-time-duration OSL fast decay fluorescence. Due to the measurement of a tenth of a nano-second, the amount of room light collected is a tenth of 1 billionth of a second or 1E-10.

Figure 2:
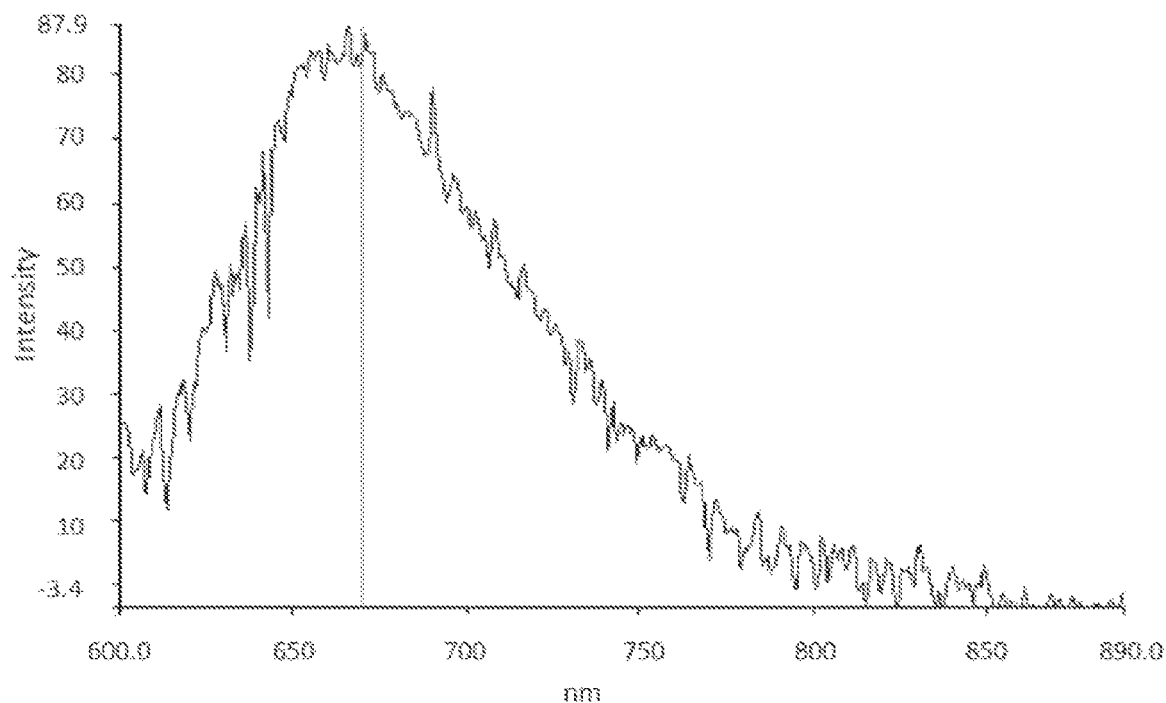
FIG. 2 shows emission spectra for a gamma irradiated nano-LiF powder in a polymer, in accordance with one embodiment of the present invention.
Figure 3:
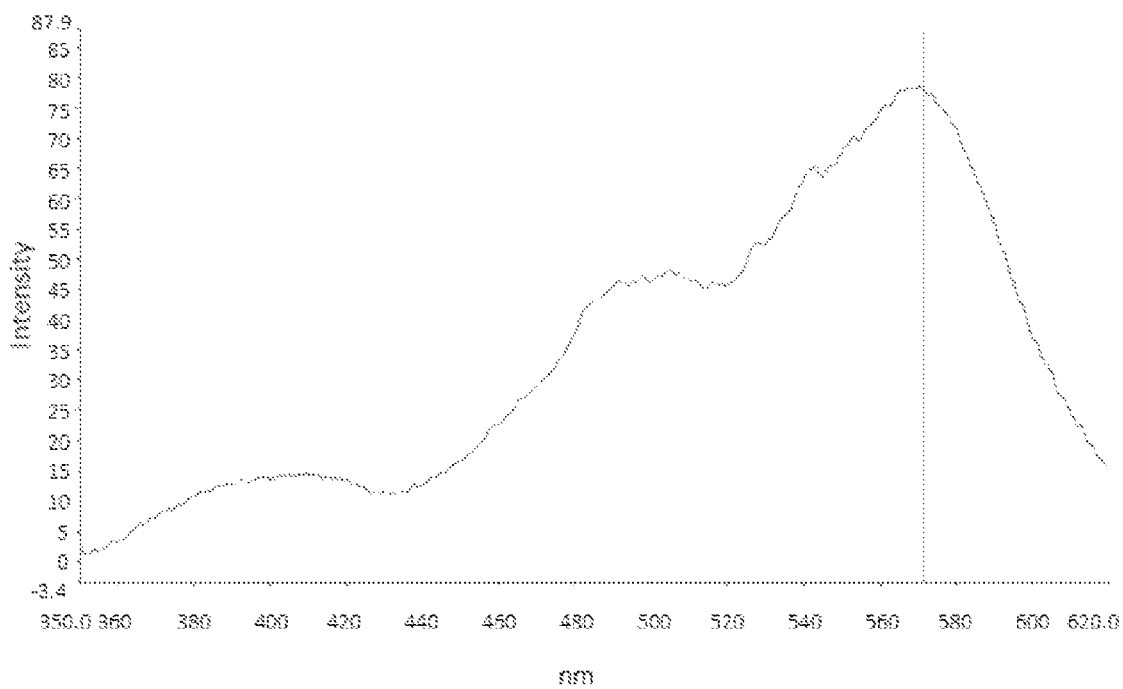
FIG. 3 shows excitation spectra for a gamma irradiated nano-LiF powder in a polymer, in accordance with one embodiment of the present invention.

The present invention also includes a method of altering properties of a luminescent material. As the size of the particle size decreases then the energetics of the trapped electron states also change and, therefore, as the size of the particles get very small the material time constant of the emission also changes. As an example, preparing or grinding LiF crystals to very small particle sizes—from approximately 1 to 2,000 nanometers—and by using alcohol solution to trap and suspend the smallest particles of LiF while separating the larger particles (that settled quickly to the bottom) generated 200 nm and smaller LiF crystals. These small LiF particles were then mixed with polyethylene and irradiated. The very small, irradiated LiF nanoparticles, many of which were in the 10-100 nanometer range, exhibited much disrupted optical properties. Instead of the typical green and red emissions upon blue excitation, a single bright 665-670 nm red emission was measured, as shown in FIG. 2, with three excitation peaks with maxima at approximately 400 nm, 495 nm, and 570 nm, as shown in FIG. 3.

Gamma-irradiated macro LiF particles in polymers (e.g., polyethylene) in the size range of tens of microns produce stable bright green (~535 nm) and red (~650 nm) emission with blue (~450 nm) excitation.

Adding 1-5 micron gamma-irradiated LiF powder to polymers produces very bright (~750 nm) IR emission.

High-pressure treatment of LiF single crystals, followed by ionizing radiation exposure, produces intense (~1200-1700 nm) IR emission. After pressing, the LiF can be ground and added to various binding materials such as polymer, adhesives, etc. IR emission is stable and proportional to ionizing radiation dose over a wide range. Most visible wavelengths can be used to excite the IR emission.

Greater than 1200 nm IR properties are more heat-sensitive than the green and red emissions and therefore can be eliminated by a heat-treatment to about 300° C. for approximately 15 to 30 minutes.

Potential uses of the various embodiments of the Present Invention include, but are not limited to, at least the following: optical data storage; security marking/tagging, optical computing, radiation dosimetry, and light detection.

The present invention has been described in terms of specific embodiments incorporating details to facilitate the understanding of the principles of construction and operation of the invention. As such, references herein to specific embodiments and details thereof are not intended to limit the scope of the claims appended hereto. It will be apparent to those skilled in the art that modifications can be made in the embodiments chosen for illustration without departing from the spirit and scope of the invention.

I claim:

1. A method of measuring luminescence of a material, comprising:
   a. applying a light source to excite an exposed, irradiated material;
   b. amplifying an emission signal of the material; and
   c. measuring a luminescent emission at a fixed time window of about 10 picoseconds to about 10 nanoseconds, wherein an excitation pulse of the light source is an approximately 10 picosecond to 300 picosecond wide pulse, and wherein the material is an alkali halide, alkali earth halide, glass, or combinations thereof.

2. The method of claim 1 wherein the luminescence is one of the following: radio photoluminescence (RPL) and optically stimulated luminescence (OSL).

3. The method of claim 1 wherein the light source is one of the following: a laser, a light-emitting diode (LED), and a flash lamp.

4. The method of claim 1 further comprising filtering to isolate a desired range of emission wavelengths.

5. The method of claim 1 wherein an excitation pulse of the light source is shorter than a decay time constant of the material.

6. The method of claim 5 wherein the decay time constant is a sub-nano-second decay constant.

7. The method of claim 6 wherein the decay time constant is in the range of 100 to 300 picoseconds.

8. The method of claim 1 wherein a train of light pulses is applied repeatedly to quantify a radiation dose imparted to the material.

9. The method of claim 1 wherein the alkali halide material is lithium fluoride.

10. The method of claim 9 wherein the alkali halide material is combined with a polymer.

11. The method of claim 1 wherein the alkali halide material is at least one of the following: sodium fluoride, a bromide, a chloride, and an iodide.

12. The method of claim 11 wherein the alkali halide material is combined with a polymer.

13. The method of claim 1 wherein the material is in the size range of approximately 10 nanometers to approximately 500 micrometers.

14. A method of altering properties of a luminescent material, comprising:
   a. preparing the luminescent material to a size range of approximately 1 to 2,000 nanometers, wherein the luminescent material is an alkali halide, alkali earth halide, glass, or combinations thereof;
   b. irradiating the material; and
   c. exciting the irradiated material with a pico-second pulse from a light source to measure at least one of the following altered properties of the material: excitation curves, emission curves, and a time constant of a luminescent emission of the material.

15. The method of claim 14 wherein the alkali halide material is lithium fluoride.

16. The method of claim 14 wherein the alkali halide material is at least one of the following: sodium fluoride, a bromide, a chloride, and an iodide.

17. The method of claim 14 wherein the light source is one of the following: a laser, a LED, and a flash lamp.

18. The method of claim 14 wherein the time constant includes more than one time constant.

* * * * *